(12) United States Patent
Rosén et al.

(10) Patent No.: US 6,658,284 B1
(45) Date of Patent: Dec. 2, 2003

(54) DEVICE FOR REDUCING SIGNAL NOISE IN A FETAL ECG SIGNAL

(75) Inventors: Karl G. Rosén, Kungalv (SE); Arne Samuelsson, Moelndal (SE)

(73) Assignee: Neoventa Medical AB, Gothenburg (SE)

( * ) Notice: Subject to any disclaimer, the term of this patent is extended or adjusted under 35 U.S.C. 154(b) by 0 days.

(21) Appl. No.: 09/530,207

(22) PCT Filed: Dec. 22, 1999

(86) PCT No.: PCT/GB99/04371

§ 371 (c)(1),
(2), (4) Date: Apr. 26, 2000

(87) PCT Pub. No.: WO00/36975

PCT Pub. Date: Jun. 29, 2000

(30) Foreign Application Priority Data

Dec. 22, 1998 (GB) ............................................. 9828362

(51) Int. Cl.[7] ............................................. A61B 5/0444
(52) U.S. Cl. ....................................................... 600/511
(58) Field of Search ................................ 600/373, 376, 600/377, 383, 509, 511, 515, 516, 517, 519; 607/116, 139

(56) References Cited

U.S. PATENT DOCUMENTS

| | | | |
|---|---|---|---|
| 3,703,168 A | * 11/1972 | Frink | |
| 4,211,237 A | 7/1980 | Nagel | |
| 5,042,499 A | 8/1991 | Frank et al. | |
| 5,372,139 A | * 12/1994 | Holls et al. | 128/698 |
| 5,469,856 A | 11/1995 | Lundstrom et al. | |
| 5,596,993 A | * 1/1997 | Oriol et al. | 128/698 |
| 5,623,939 A | 4/1997 | Garfield | |
| 5,704,365 A | * 1/1998 | Albrecht et al. | 128/702 |

FOREIGN PATENT DOCUMENTS

| | | |
|---|---|---|
| EP | 0310349 | 4/1989 |
| GB | 1 410 939 | 10/1975 |
| GB | 1 605 051 | 12/1981 |
| GB | 2 162 644 | 2/1986 |
| WO | WO96/08996 | 3/1996 |

* cited by examiner

Primary Examiner—Jeffrey R. Jastrzab
Assistant Examiner—Frances P. Oropeza
(74) Attorney, Agent, or Firm—McCormick, Paulding & Huber LLP

(57) ABSTRACT

Apparatus for reducing signal noise in a fetal ECG signal obtained by using a unipolar ECG lead configuration 1, 3 thereby detecting a predominant T wave vector and avoiding changes in ECG waveform shape due to fetal rotation through the birth canal. The ECG signal is transmitted by means of a first signalling link 5 to the signal noise reducing components which include a conventional analogue filter 7, a digital high pass filter 9 for attenuating low frequencies and with a predetermined cut-off frequency, the cut-off frequency being essentially between 0.2 and 1.7 Hz, and a further digital filter 11. The filtered ECT signal is arranged as output signal from the electrical arrangement by means of a second signalling link 13.

21 Claims, 4 Drawing Sheets

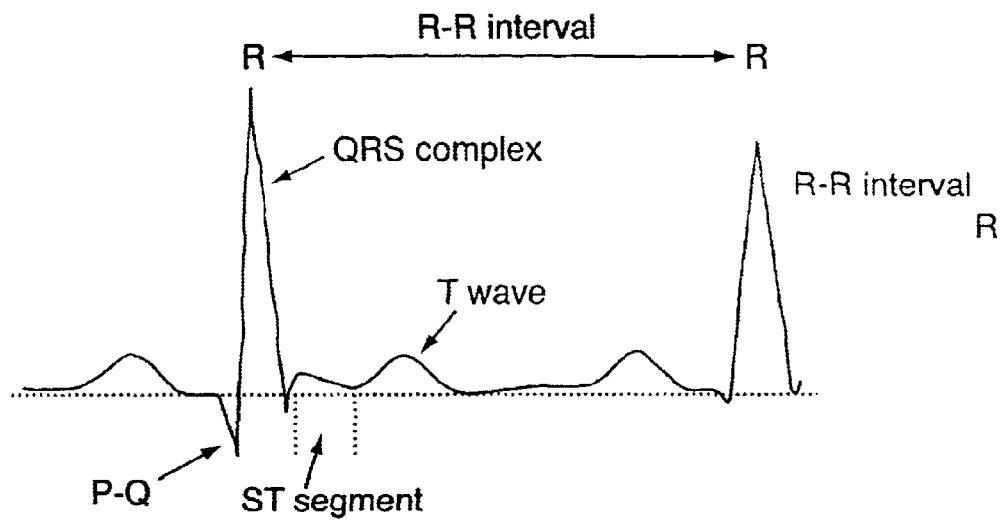
FIG. 1
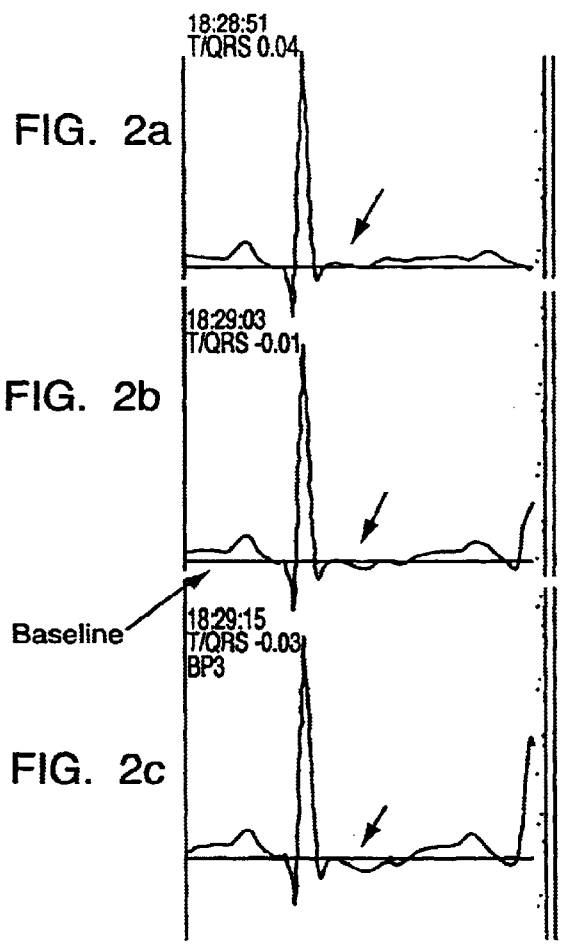
FIG. 2a
FIG. 2b
FIG. 2c

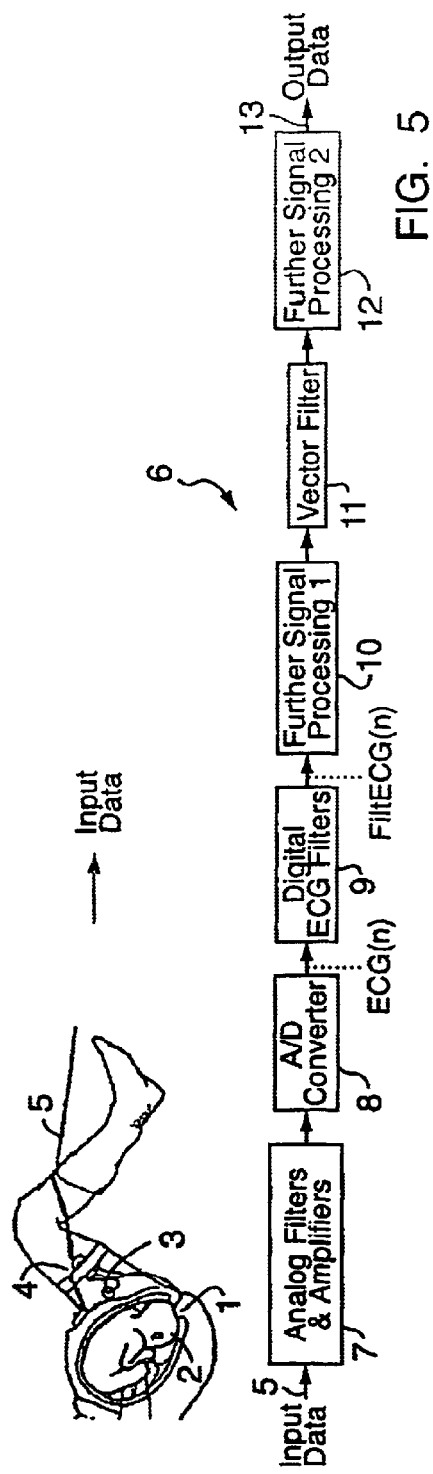
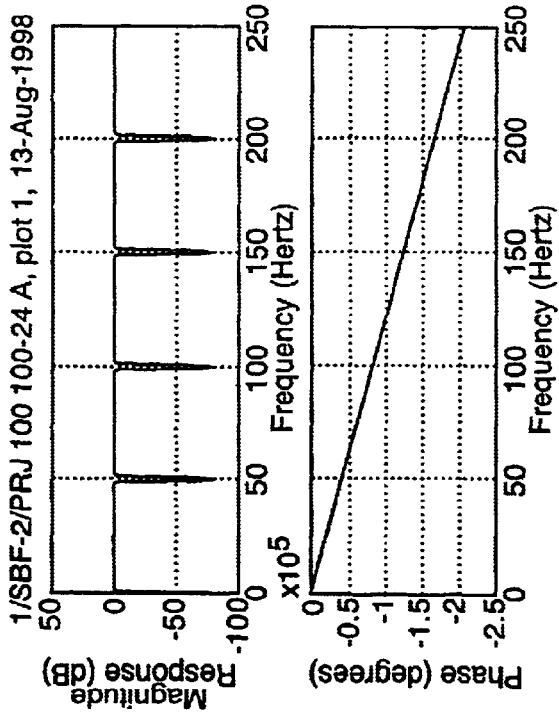
FIG. 5
FIG. 6

DEVICE FOR REDUCING SIGNAL NOISE IN A FETAL ECG SIGNAL

BACKGROUND ART

The present invention relates to a method and apparatus for reducing signal noise in a fetal ECG signal, typically one obtained by using a unipolar ECG lead configuration which detects a predominant T wave vector whilst avoiding changes in ECG waveform shape due to fetal rotation through the birth canal.

Fetal surveillance during labour is standard clinical practice. The purpose is to identify abnormal events and fetal oxygen deficiency in particular. Since its introduction in the sixties it has been evident that electronic fetal monitoring by fetal heart rate analysis alone does not provide all the information required for an optimal identification of a fetus suffering from lack of oxygen.

During the last 20 years work has been ongoing to clarify what fetal signals could be made use of to provide additional information. Since the early seventies, waveform analysis of the fetal electrocardiogram has been studied from both physiological, signal processing and clinical aspects (Rosen KG: Fetal ECG waveform analysis in labour. Fetal monitoring. Physiology and techniques of antenatal and intrapartum assessment. ad. Spencer JAD). Castle House Publications. pp. 184–187,1989). It was found that the ST interval and T-wave amplitude were of particular interest.

FIG. 1 depicts two consecutive heart beats with the different ECG components of interest during foetal surveillance being identified. It has been found that changes in the ST interval of the Fetal Electro CardioGram (ECG) are part of the components that reflect the stress of the fetal heart during the labour. Basically, the changes that appear in the ST interval due to lack of oxygen, can be divided into 3 classes:
1. ST rise with increased ST segment and T wave amplitude;
2. Appearance of so called biphasic ST changes, with an ST segment with a negative slope;
3. Appearance of negative T waves.

These discoveries have been applied in a clinical trial in which the ST-waveform (ie. the ST segment plus the T wave) of the fetal electrocardiogram was shown to provide more useful information than the mere detection of RR-intervals (fetal heart rate) (Westgate J, M Harris, J S H Curnow, R R Greene: Plymouth randomised trial of cardiotocogram only versus ST waveform plus cardiotocogram for intrapartum monitoring; 2400 cases. Am J Obstet Gynaecol 169(1993)1151).

Several problems regarding the fetal ECG-signal quality have been identified over the years. Clearly, it is a prerequisite to be able to detect the ST waveform, and so one of the main requirements for ST-waveform analysis of the fetal electrocardiogram is a fetal ECG lead configuration that is consistent and allows the identification of the T vector during labour.

The conventional ECG level configuration used for fetal monitoring is the bipolar fetal ECG lead configuration. Here, both exploring electrodes are located close to each other on the presenting part of the fetal body, ie. the head or buttock. As a consequence of the location of the electrodes, there is a maximum sensitivity to ECG waveform changes with a main vectorial distribution in the horizontal plane of the fetus. However, experimental data have shown a maximal representation of T wave vector along the longitudinal axis of the fetus. Thus, the standard fetal ECG lead, well suited when only using the R wave for fetal heart rate detection, will not enable the accurate detection of changes in T wave amplitude.

This can only be done by constructing an ECG lead that is sensitive to ECG waveform changes appearing in the longitudinal axis of the fetus. It is known from the literature that the use of a unipolar fetal ECG lead configuration enables the detection of the main T-wave vector more accurately then the standard bipolar ECG lead configuration (Lindecrantz K, Lilja H, Widmark C, Rosen KG: The fetal ECG during labour. A suggested standard. J. Biomed. Eng. 1988; 10: 351–353). In this configuration, one of the exploring electrodes is located well away from the fetus, e.g. on the maternal skin. The maternal thigh has been found to be a suitable place. The other exploring electrode is the standard scalp electrode needle placed under the skin of the presenting fetal part.

A further problem is the existence of signal noise which is far more significant when the S-T waveform is being studied than is the case with conventional fetal ECG monitoring. An illustration of progressive changes in the ST segment of the foetal ECG recorded during labour is presented in FIGS. 2a–c. The ECG baseline as indicated by the present invention is depicted as well. The appearance of biphasic changes in the ST segment follows a pattern, which is exemplified in FIGS. 2a–c. This is a sequential recording showing 30-beat ECG averages. As seen in FIGS. 2a–c, the ST segments are classified in a 3-level scale that reflects the relation between the negative slope of the ST segment compared to the baseline of the ECG. As will be appreciated, to be able to perform this type of analysis, a very high signal quality regarding low frequency noise is required.

Although the unipolar fetal ECG electrode configuration discussed above enables the T vector to be identified, a signal noise problem is generated at the same time. The maternal skin electrode is sensitive to maternal movements causing both low frequency (movement artifacts) and high frequency (muscular activity) noise. Another source of noise is the interference from mains frequencies.

Thus, the sources of signal noise may be summarised as:
A. High frequency components related to muscle activity.
B. Interference from mains frequencies.
C. Low frequency noise largely generated by fetal and maternal movements Any system for assessment of the ST-waveform of the fetal electrocardiogram has to reduce the interference from these potential sources of signal noise, but obviously, any techniques applied to reduce signal noise should not significantly interfere with the ST waveform. Furthermore, the signal processing should be done continuously as the state of oxygen delivery to the fetus can change from one minute to another and any delay in the presentation of ECG-waveform data would be disadvantageous.

The technique used in the Plymouth trial (westgate et al, 1993) used analogue filtering signal processing undoubtedly with some success. However, there were limitations to what can be achieved. The fetal scalp ECG signal amplitude (QRS complex) varies normally between 100 and 400 $\mu$V but the T wave is normally only 1/10 of an amplitude of the peak signal and so great care has to be taken not to interfere with this low amplitude part of the signal. The use of analogue high pass filters to reduce low frequency (ie. below 1 Hz) baseline shifts carries the risk of markedly affecting the T wave amplitude and guidelines instituted by the American Heart Association recommend a low frequency cut-off of only 0.05 Hz (Electrocardiography recommendations for the standardization of leads and of specifications for instruments in ECG/VCG circulation. American Heart Association Committee, 1975, Pp 1–25). These guidelines were followed in the Plymouth trial.

As a consequence, the prior art analogue filtering techniques will, to only a very limited extent reduce low frequency noise generated by electrode movements and the data interpretation has therefore been limited to more robust changes. There is therefore a need to improve the quality of the fetal electrocardiogram to enable continuous and detailed assessment of ST-waveform changes during labour.

SUMMARY OF THE INVENTION

According to the present invention there is provided a method of reducing noise in a fetal ECG signal comprising connecting electrodes to the fetus and the maternal skin in a unipolar configuration and feeding the signal detected by said electrodes through a first high pass filter, the cut-off frequency of the first high pass filter being between 0.2 and 2.7 Hz.

The invention also provides an apparatus for obtaining a fetal ECG signal comprising exploring electrodes for connection to the fetus and the maternal skin in a unipolar configuration in order to detect an ECG signal and a signal noise reducing device linked to the electrodes by means of a first signalling link, wherein the signal noise reducing device comprises a first high pass filter, the cut-off frequency of the first filter being between 0.2 and 2.7 Hz.

Typically, one electrode is attached to the fetal scalp and one is attached to the maternal thigh.

The "cut-off frequency" as used herein refers to the frequency below which a significant degree of signal attenuation e.g. −3 dB, takes place. In preferred forms of the invention there may be as little as 0.1 dB attenuation in most of the pass band and around 40 dB attenuation in most of the stop band.

Thus, it will be seen that the invention provides signal filtering using a far higher cut-off frequency than that thought possible in the prior art. This is based upon a recognition that, although the baseline fluctuations of the ECG signal (due to movements, breathing, impedance variations etc.) can have a significantly higher amplitude than the ST waveform, most of the energy of the baseline fluctuation is at a lower frequency range than the frequency range of the ST interval. This is illustrated in the spectrum shown in FIG. 3. Thus, the invention provides a signal quality enhancement model that allows the accurate presentation of ECG waveform changes within the ST interval frequency.

The signal may be fed directly from the electrodes to the noise reducing device of the invention, or it may be pre-filtered, e.g. using the prior art apparatus discussed above such as an analogue band pass filter having cut-off frequencies of about 0.05 and 100 Hz. The former cut-off serves to eliminate DC levels and very low frequency components that might otherwise decrease the dynamic range of the signal.

In the device of the invention, a cut-off frequency of up to 2.7 Hz has been found satisfactory in that the T/QRS ratio is largely unaffected when the fetal heart rate is over 100 beats/min. However, in order to provide satisfactory performance with lower heart rates, it is preferred that the cut-off frequency is less than 1.7 Hz. To optimise noise reduction, the cut off frequency is preferably greater than 0.7 Hz and around 1.2 Hz is believed to be the most effective cut-off frequency overall.

The first high pass filter may be an analogue filter, but it is highly desirable that this filter should add the minimum of phase distortion and so it is believed that this invention may more readily be achieved using digital techniques, in which case the signal is digitised before being passed through the first high pass filter.

As discussed above, another source of signal noise is interference from mains frequencies. In order to decrease the influence of mains, the device preferably also comprises a notch mains frequency filter for attenuating the mains frequency contents of the ECG signal, the notch mains frequency filter preferably being applied to the ECG signal in connection with the first high pass filter. The notch mains frequency filter is arranged to correspond to the local mains frequency, for example 50 Hz or at 60 Hz. Since modern digital filters may improve signal/noise ratio substantially without causing unwanted changes in signal waveform a multitude of digital filters may be used with very narrow cut-offs to reduce interference from both low and high frequencies as well as mains noise.

The noise reducing steps described above may be combined with further steps. For example, one technique for performing noise reduction of a repetitive signal is to use averaging with equal or weighted coefficients. However, there are limitations and as an example, ECG complexes with marked baseline shift may corrupt the averaged complex causing erroneous information to be generated. It would therefore be advantageous if as much as possible of signal noise could be eliminated prior to such signal averaging.

Even modern digital (in this case high-pass) filters, may leave a part of the low frequency noise in the signal which, during an R-R interval, can be seen as a baseline shift or slope. This deviation in the available signal, compared to the real ECG, may in some circumstances make a qualified analysis of the ST segment difficult. Therefore, the invention preferably also includes a step in which residual low frequency noise of the continuous ECG signal is attenuated further using vector subtraction principles. An advantage with such a filter is the ability to operate immediately after a possible loss of signal with the ECG signal exceeding the dynamic range.

Thus, preferably a second high pass filter is provided for further attenuation of signal noise in a digitised fetal ECG signal where the signal noise is primarily constituted by baseline fluctuations of the ECG signal. The ECG signal typically comprises a sequence of ECG complexes in the form of uncompensated samples, each ECG complex including a QRS complex, the second high pass filter being arranged after the cutoff frequency high pass filter, the additional high pass filter comprising: means for identifying ECG complexes of the ECG signal and their P-Q points; means for obtaining an approximating function to a curve between one P-Q point and a proceeding or a succeeding P-Q points by using a number of proceeding and succeeding P-Q points, the number being at least one; and means for forming the compensated samples to an output signal.

One way of implementing the vector subtraction is that the means for obtaining an approximating function to the curve is arranged for determination of slopes of lines between P-Q points and proceeding or succeeding P-Q points; and compensated values y[i] are obtained according to: y[i]=x[i]−m−k(i−ipq), where i, x[i], m, k and ipq denote index for each sample, uncompensated sample with index i, the level of the P-Q point for the present complex, the slope for the present complex, the index for the P-Q point sample, respectively.

In case a first degree polynomial is not sufficient, it is possible that the means for obtaining an approximating function to the curve is arranged for determination of polynomials of higher degree than one, the polynomials being based on a P-Q point and proceeding and/or succeeding P-Q points.

In some circumstances, it may be possible to provide a signal of such quality that signal averaging would be unnecessary. However, when this is not the case, it may be advantageous if the device also comprises an averaging filter which is preferably applied to the ECG signal in connection with the second high pass filter. Preferably averaging takes place over twenty to thirty cycles. A larger number risks causing appreciable attenuation to the height of the T wave.

BRIEF DESCRIPTION OF THE DRAWINGS

An embodiment of the invention will now be described, by way of example only, and with reference to the accompanying drawings:

FIG. 1 depicts two consecutive heart beats with the different ECG components of interest to the present invention for foetal surveillance.

FIGS. 2a–2c present an illustration of progressive changes in the ST segment of the foetal ECG recorded during labour. The ST segments are indicated by arrows. The ECG baseline indicated by the present invention is also depicted.

FIG. 5 presents a block diagram of the noise reducing device of the embodiment.

FIG. 6 presents a graph relating to complete frequency spectrum of a preferred embodiment of a filter of the present invention, this filter being a 1.5 Hz high pass (multi-notch) filter.

DETAILED DESCRIPTION OF PREFERRED EMBODIMENTS

Figure 3:
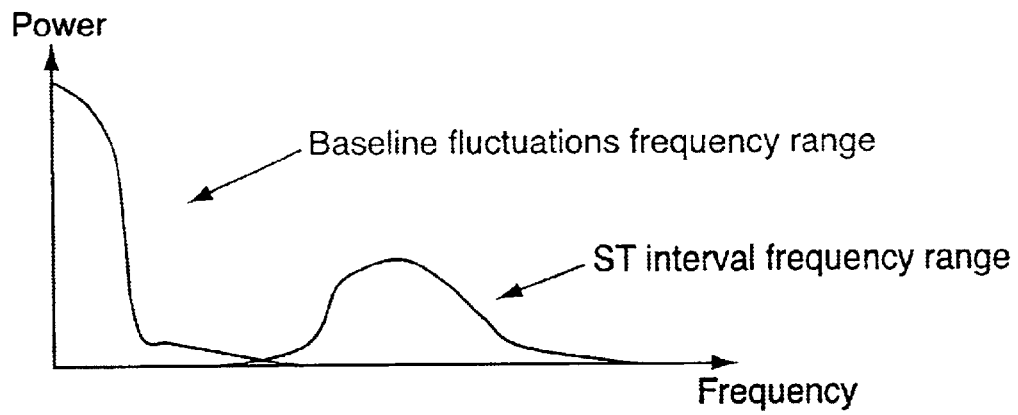
FIG. 3 presents an exemplary spectrum including baseline fluctuations and an ST interval frequency ranges.

Turning first to FIG. 5 there is provided an over-view of a fetal monitoring apparatus in use. A first electrode 1 is attached to the head 2 of the fetus and a second electrode 3 is attached to the maternal thigh 4. Electrode leads 5 transmit the detected ECG signal to the noise reducing device (shown generally as 6), the structure of which is described in more detail below. A further set of leads 13 transmits the output from the device 4 to display apparatus such as a monitor (not shown).

The first stage 7 of the noise reducing device contains conventional analogue filters for reducing DC and low frequency components of the signal. The cut-off frequency of this stage is 0.05 Hz. This stage also contains a 100 Hz low pass filter for removing comparatively high frequency components.

The first stage serves to reduce the requirements of the next stage 8 which is an analogue to digital converter, operating at 500 Hz.

The digitised signal is then fed to a first digital ECG filter stage 9 which has a 1.2 Hz cut-off frequency (for 3 dB attenuation) and which attenuates the signal by less than 0.1 dB above 1.5 Hz. It also contains notch filters for removing mains supply interference. This stage is discussed more fully below.

Subsequently, the signal is processed further in stage 10. This serves to detect the QRS complexes in the ECG signal and to define their PQ points. In combination with vector filter 11, this enables residual low frequency noise to be removed by means of the vector subtraction process previously described.

The final part of the device 6 is stage 12 which performs the calculation of HR values, ECG averaging and ECG waveform analysis in the known manner before the output data is transmitted via leads 13 to a display screen and/or a printer.

Figure 7:
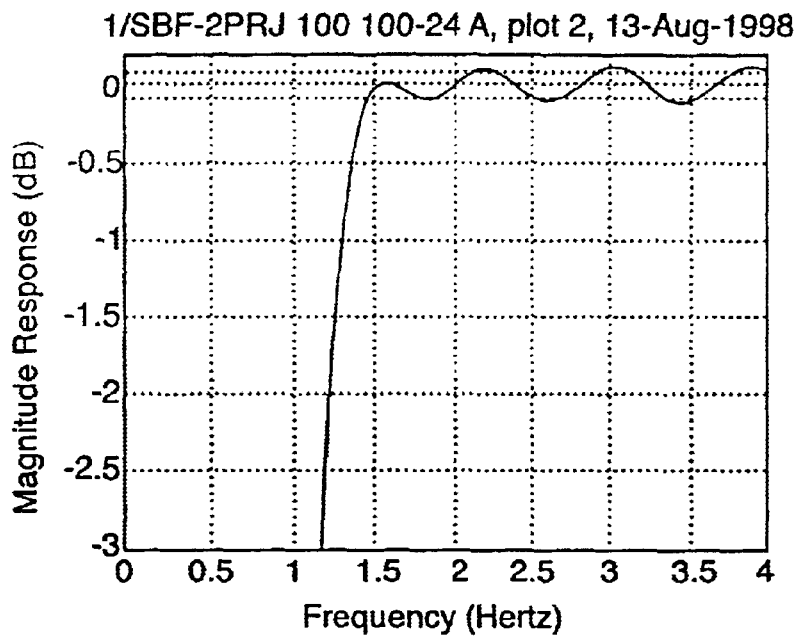
FIG. 7 presents a graph relating to a first cut off region of a preferred embodiment of a filter of the present invention, this filter being a 1.5 Hz high pass (multi-notch) filter.

As previously discussed, the ECG filter section 9 comprises a high-pass filter, with a cut-off frequency of 1.2 Hz and includes other notch stop bands for mains supply noise rejection. It is phase-linear (i.e. it has constant group delay) in the pass band. FIGS. 6 and 7 illustrate the characteristics of this filter section.

The filter can be realised in a number of ways. Two examples are:

1. A FIR-filter consisting of one or several serial stages.

OR

Figure 8:
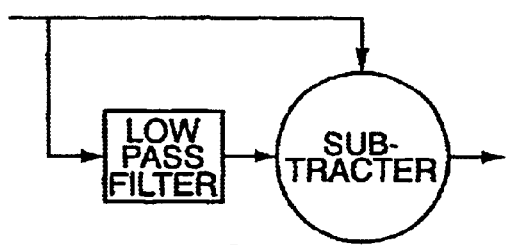
FIG. 8 depicts a subtraction filter to be used in the embodiment.

2. A 'subtraction filter', where the output signal is simply the input signal with the noise subtracted in the time domain. The noise is the result of a filter with the inverse frequency response compared to the figure above, see FIG. 8.

One example of the first type of filter is a two stage serial FIR filter with the two following transfer functions. An example of this kind of filter is presented in FIG. 9.

Figure 9:
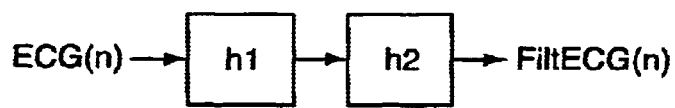
FIG. 9 depicts a two stage filter used in the embodiment.

The h1 block presented in FIG. 9 is a FIR filter with the following transfer function:

$$y(n) = \sum_{i=0}^{i<N1} ECG(n-i) \cdot h1(i)$$

The h2 block presented in FIG. 9 is a FIR filter with the following transfer function:

$$Filt\ ECG(n) = \sum_{i=0}^{i<N2} y(n-i) \cdot h2(i)$$

FIGS. 6 and 7 show the high-pass cut-off frequency at 1.2 Hz for 3 dB attenuation. Apart from this cut-off characteristic, there is a lot of characteristics that affect the N1 and N2 values and the related coefficients, such as:

Ripple in the pass band.

Attenuation in the stop band.

Slope of the frequency response from stop band to pass band, i.e. how wide is the stop band (it can not be equal to the 1.2 Hz above, would result in an indefinite number of coefficients for a digital filter).

In addition, the transfer functions will be affected (possibly resulting in simpler implementations) if notch stop band are used or not, or if the characteristic of the notches are related to the characteristic of the first high-pass cut-off region.

Therefore, no absolute setup of coefficients is relevant, but the main characteristic is the high-pass cut-off frequency (at some attenuation level), as illustrated in FIG. 7 to 1.2 Hz.

An experimental comparison of embodiments of the present invention with noise reducing devices having different high pass filters has been carried out. This was done by applying a series of digital filters to a set of stored fetal ECG data with the following characteristics:

The ECG is recorded from a skin and a scalp electrode.

The ECG signal has passed an analogue band pass filter with cut-off frequencies of 0.05 and 100 Hz.

The analogue ECG is sampled and AD converted with 500 Hz.

Distinct changes in the ST interval with increasing T/QRS at varying foetal heart rate levels.

The reason for testing at different foetal heart rate levels is the marked fluctuations that may occur and we can assume that the frequency range of the ST interval may change depending on heart rate.

The following filters with minimum phase distortion were applied:
1. No digital filters used at all (TQRS–0 Hz).
2. Multi notch N2 with pass band 0–48.5, 51.5–148.5 Hz etc. Additional HPl multi notch with pass band 0.5–124.5 Hz, 125.5–249.5 Hz (TQRS–½ Hz).
3. Multi notch N2 with pass band 0–48.5, 51.5–148.5 Hz etc. Additional HPl multi notch with pass band 1–124 Hz, 126–249 Hz (TQRS–1 Hz).
4. Multi notch with pass band 1.5–48.5 Hz, 51.5–98.5 Hz, 101.5–148.5 Hz etc (TQRS–1½ Hz).
5. Same as filter no. 4 regarding 50 Hz and overtones, but additional multi notch pass band 2–123 Hz and 127–248 Hz (TQRS–2 Hz).
6. Same as filter no. 4 regarding 50 Hz and overtones, but additional multi notch pass band 2.5–122.5 Hz, 127.5–247.5 Hz (TQRS–2½ Hz).
7. Same as filter no. 4 regarding 50 Hz and overtones, but additional multi notch pass band 3–122 Hz, 128–247 Hz (TQRS–3 Hz).

In this experiment, the pass bands are regarded as those frequencies where less than 0.1 dB attenuation occurs. As may be seen from FIG. 7, the frequency response typical of the filters used is such that the cut-off frequency defined with reference to 3 dB attenuation is approximately 0.3 Hz lower. In the case of the notch filters, the upper end of the pass band is approximately 0.3 Hz higher for 3 dB than for 0.1 dB attenuation.

Figure 4:
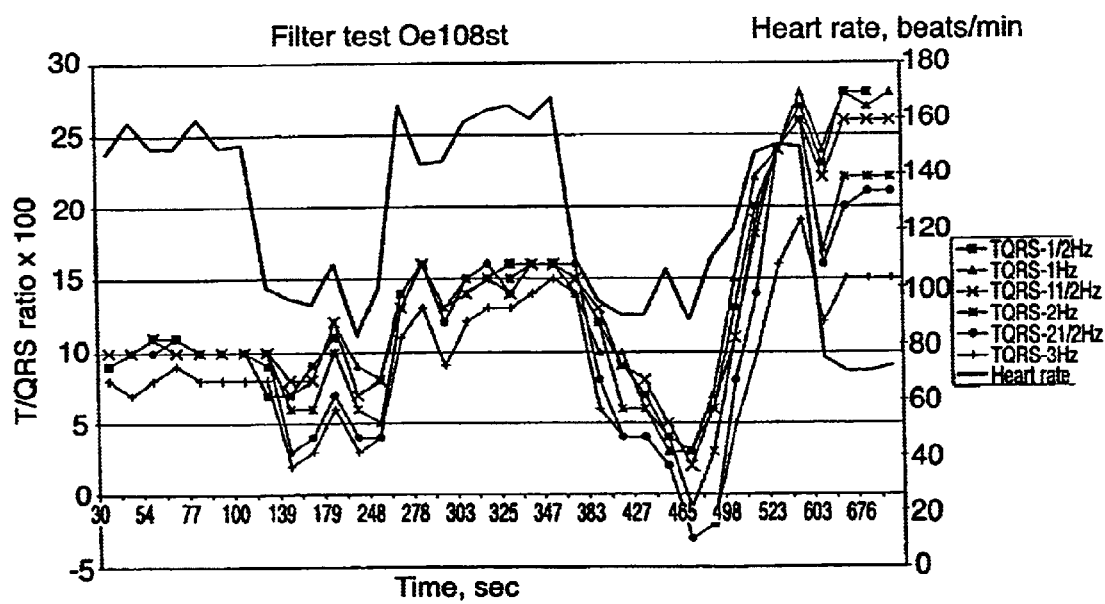
FIG. 4 presents an illustration of the impact of high pass filtering on T wave amplitude quantified by the T/QRS ratio, at different fetal heart rate levels.

The following can be found from examining the data displayed in FIG. 4. The frequencies in parentheses refer to the corresponding cut-off values for 3 dB attenuation:
1. A filter with a high pass of 3 Hz (2.7 Hz) affects the T/QRS ratio with a false lowering of the ratio recorded regardless of fetal heart rate.
2. The T/QRS ratio is largely unaffected by the high pass filters of <3.0 Hz (2.7 Hz) when ECG data are sampled at fetal heart rates>100 beats/min approximately.
3. When heart rate drops below approximately 100 beats per minute filter characteristics becomes even more important and a high pass of <2 Hz (1.7 Hz) is required not to affect the T/QRS ratio.

Thus, it may be seen that by means of the invention it is possible to attenuate fetal ECT signal noise at higher frequencies than was previously thought possible. In view of the noise frequency distribution discussed above, this allows for much greater signal noise reduction which thereby enables more reliable fetal monitoring.

What is claimed is:

1. A method of reducing noise in a fetal ECG signal, said method comprising the steps of:
   connecting electrodes to a fetus and maternal skin in a unipolar configuration; and
   feeding the signal detected by said electrodes through a first high pass filter, cut-off frequency of the first high pass filter being between 0.2 and 2.7 Hz.

2. A method as claimed in claim 1, wherein the cut-off frequency is less than 1.7 Hz.

3. A method as claimed in claim 1, wherein the signal is also fed through a notch filter, the notch filter being arranged to attenuate mains frequency contents of the signal.

4. A method as claimed in claim 3, wherein the notch filter attenuates signal components having frequencies of 50 Hz or 60 Hz.

5. A method as claimed in claim 1, wherein the signal is digitised before being passed through a second high pass filter.

6. A method as claimed in claim 5, wherein the signal comprises a sequence of ECG complexes in a form of uncompensated samples, each ECG complex including a QRS complex and the method further comprises the steps of:
   identifying ECG complexes of an ECG signal and their P-Q points;
   obtaining an approximating function to a curve between one P-Q point and a proceeding or a succeeding P-Q points by using a number of proceeding and succeeding P-Q points, the number being at least one; and
   using compensated samples to derive an output signal.

7. A method as claimed in claim 6, wherein the step of obtaining an approximating function to the curve comprises determination of slopes of lines between P-Q points and proceeding or succeeding P-Q points; and compensated values y[i] are obtained according to: y[i]=x[i]–m–k (i–ipq), where i, x[i], m, k and ipq denote index for each sample, uncompensated sample with index i, level of the P-Q point for the present complex, slope for the present complex, index for the P-Q point sample, respectively.

8. A method as claimed in claim 6, wherein the step of obtaining an approximating function to the curve comprises determination of polynomials of higher degree than one, the polynomials being based on a P-Q point and proceeding and/or succeeding P-Q points.

9. A method as claimed in claim 6, further comprising the step of passing the signal through an averaging filter associated with second high pass filter.

10. A method as claimed in claim 1, further comprising the step of displaying at least part of the filtered signal.

11. Apparatus for obtaining a fetal ECG signal comprising exploring electrodes for connection to the fetus and the maternal skin in a unipolar configuration in order to detect an ECG signal and a signal noise reducing device linked to the electrodes by means of a first signalling link, wherein the signal noise reducing device comprises a first high pass filter, cut-off frequency of the first filter being between 0.2 and 2.7 Hz.

12. An apparatus as claimed in claim 11, wherein the cut-off frequency is less than 1.7 Hz.

13. An apparatus as claimed in claim 11, wherein the signal is also fed through a notch filter, the notch filter being arranged to attenuate mains frequency contents of the signal.

14. An apparatus as claimed in claim 13, wherein the notch filter attenuates signal components having frequencies of 50 Hz or 60 Hz.

15. An apparatus as claimed in claim 13, wherein the signal is subsequently digitised before being passed through a second high pass filter.

16. An apparatus as claimed in claim 15, wherein the second high pass filter comprises:
   means for identifying ECG complexes of the ECG signal and their P-Q points;
   means for obtaining an approximating function to a curve between one P-Q point and a proceeding or a succeeding P-Q points by using a number of proceeding and succeeding P-Q points, the number being at least one; and means for using compensated samples to derive an output signal.

17. An apparatus as claimed in claim 16, wherein the means for obtaining an approximating function to the curve is arranged for determination of slopes of lines between P-Q points and proceeding or succeeding P-Q points; and compensated values y[i] are obtained according to: $y[i]=x[i]-m-k(i-ipq)$, where i, x[i], m, k and ipq denote index for each sample, uncompensated sample with index i, level of the P-Q point for the present complex, slope for the present complex, index for the P-Q point sample, respectively.

18. An apparatus as claimed in claim 16, wherein the means for obtaining an approximating function to the curve is arranged for determination of polynomials of higher degree than one, the polynomials being based on a P-Q point and proceeding and/or succeeding P-Q points.

19. An apparatus as claimed in claim 16, further comprising an averaging filter associated with the second high pass filter.

20. An apparatus as claimed in claim 1, further comprising means for displaying at least part of a noise-reduced signal.

21. An apparatus for reducing noise in a fetal ECG signal comprising a first high pass filter having a cut-off frequency between 0.2 and 2.7 Hz and a second high pass filter comprising means for identifying ECG complexes of an ECG signal and their P-Q points;

means for obtaining an approximating function to a curve between one P-Q point and a proceeding or a succeeding P-Q points by using a number of proceeding and succeeding P-Q points, the number being at least one; and means for using compensated samples to derive an output signal.

* * * * *